(12) United States Patent
Kamei et al.

(10) Patent No.: US 9,554,769 B2
(45) Date of Patent: Jan. 31, 2017

(54) APPARATUS FOR ASSESSING RISK OF CEREBROVASCULAR DISEASES

(75) Inventors: Tsutomu Kamei, Izumo (JP); Kohji Murata, Hikawa-gun (JP); Takahiko Nakamura, Chiba (JP)

(73) Assignee: SEIKO INSTRUMENTS INC., Chiba (JP)

( * ) Notice: Subject to any disclaimer, the term of this patent is extended or adjusted under 35 U.S.C. 154(b) by 599 days.

(21) Appl. No.: 12/963,292

(22) Filed: Dec. 8, 2010

(65) Prior Publication Data

US 2011/0077533 A1 Mar. 31, 2011

Related U.S. Application Data

(63) Continuation of application No. PCT/JP2009/060630, filed on Jun. 10, 2009.

(30) Foreign Application Priority Data

Jun. 12, 2008 (JP) ................................ 2008-154262

(51) Int. Cl.
*A61B 5/02* (2006.01)
*A61B 8/06* (2006.01)
(Continued)

(52) U.S. Cl.
CPC ................ *A61B 8/06* (2013.01); *A61B 5/021* (2013.01); *A61B 5/4064* (2013.01);
(Continued)

(58) Field of Classification Search
CPC ............. A61B 8/06; A61B 5/02; A61B 5/021; A61B 5/026
(Continued)

(56) References Cited

U.S. PATENT DOCUMENTS 6,277,082 B1 * 8/2001 Gambale ....................... 600/549
6,692,443 B2 * 2/2004 Crutchfield et al. ........... 600/504
(Continued)

FOREIGN PATENT DOCUMENTS

JP 2001-079002 A 3/2001
JP 2006-204432 A 8/2006
(Continued)

OTHER PUBLICATIONS

Wikipedia.org: Hypertension and Cerebrovascular Disease.*
(Continued)

*Primary Examiner* — Jacqueline Cheng
*Assistant Examiner* — Puya Agahi
(74) *Attorney, Agent, or Firm* — Brinks Gilson & Lione

(57) ABSTRACT

The apparatus for assessing the risk of cerebrovascular diseases comprises a sensor part 1, a circuit part 2, a computation part 3 and an output part 4, where the circuit part 2 is a functional part for driving the sensor part 1 and transmitting a signal detected at the sensor part 1 to the computation part 3 and comprises a transmission circuit 21, a first receiving circuit 22, a second receiving circuit 23 and the like. The transmission circuit 21 is in connection with a transmission device 111 and a transmission device 121, for driving these devices to generate a continuous wave. A rate wave form computation part 31 is in connection with the first receiving circuit 22 and the second receiving circuit 23 to obtain the frequency of the reflected continuous wave as detected with the receiving units 112 and 122. Comparing the frequency with the frequency from the transmission circuit 21, the variation of the frequency is detected. Based on these values, blood flow rate "v" can be determined. In such manner, an apparatus for assessing the risk of cerebrovascular diseases with fewer burdens to persons to be
(Continued)

examined and with simple measurement units can be provided.

7 Claims, 6 Drawing Sheets

(51) Int. Cl.
    *A61B 5/021*     (2006.01)
    *A61B 5/00*     (2006.01)
    *A61B 8/08*     (2006.01)
    *A61B 8/04*     (2006.01)
    *A61B 5/026*     (2006.01)

(52) U.S. Cl.
    CPC ............ *A61B 5/7275* (2013.01); *A61B 8/488* (2013.01); *A61B 5/02* (2013.01); *A61B 5/026* (2013.01); *A61B 8/04* (2013.01)

(58) Field of Classification Search
    USPC ................................................ 600/485, 504
    See application file for complete search history.

(56) References Cited

U.S. PATENT DOCUMENTS

| | | | |
|---|---|---|---|
| 7,794,403 B2 * | 9/2010 | Schaafsma | 600/485 |
| 2002/0120205 A1 * | 8/2002 | Ferek-Petric | 600/513 |
| 2003/0009101 A1 * | 1/2003 | Sunagawa et al. | 600/437 |
| 2003/0097076 A1 * | 5/2003 | Nambu et al. | 600/504 |
| 2006/0184026 A1 * | 8/2006 | Nakamura et al. | 600/438 |
| 2007/0213600 A1 * | 9/2007 | John et al. | 600/300 |
| 2007/0287922 A1 * | 12/2007 | Tanaka et al. | 600/485 |
| 2008/0146951 A1 * | 6/2008 | Zhao et al. | 600/504 |
| 2009/0270734 A1 * | 10/2009 | Ragauskas et al. | 600/454 |
| 2010/0185220 A1 * | 7/2010 | Naghavi et al. | 606/158 |

FOREIGN PATENT DOCUMENTS

| | | |
|---|---|---|
| JP | 2006-204722 A | 8/2006 |
| JP | 2007-105207 A | 4/2007 |
| JP | 2007-111244 A | 5/2007 |
| JP | 2007-111245 A | 5/2007 |

OTHER PUBLICATIONS

White Matter Signal Abnormalities in Normal Individuals: Correlation with Carotid Ultrasonography, Cerebral Blood Flow Measurements, and Cerebrovascular Risk Factors, American Heart Association, 1988, pp. 1285-1288.*

Waldemar et al., White matter magnetic resonance hyperintensities in dementia of the Alzheimer type: morphological and regional cerebral blood flow correlates, 1994, pp. 1458-1465.*

* cited by examiner

FIG. 6

| HEAD MRI | GROUP WITHOUT FINDINGS | GROUP WITH FINDINGS | ρ-value |
|---|---|---|---|
| n (M/F) | 26 (14/12) | 17 (11/6) | N.S. |
| Age (years) | 64.6 ± 5.0 | 66.3 ± 9.8 | N.S. |
| BMI(kg/m$^2$) | 23.6 ± 2.4 | 22.2 ± 2.2 | N.S. |
| SBP(mmHg) | 136.8 ± 18.8 | 139.4 ± 24.9 | N.S. |
| DBP(mmHg) | 80.8 ± 11.8 | 81.1 ± 10.6 | N.S. |
| Ht (%) | 41.9 ± 3.6 | 42.9 ± 4.2 | N.S. |
| TC (mg/dl) | 206.5 ± 29.3 | 210.4 ± 35.7 | N.S. |
| HDL-C (mg/dl) | 60.0 ± 10.5 | 65.1 ± 15.3 | N.S. |
| LDL-C (mg/dl) | 120.3 ± 19.3 | 122.7 ± 31.4 | N.S. |
| TG (mg/dl) | 133.6 ± 89.9 | 111.6 ± 42.6 | N.S. |
| FBS (mg/dl) | 110.9 ± 32.9 | 121.3 ± 61.0 | N.S. |
| HbA1c (%) | 5.7 ± 1.0 | 5.7 ± 1.1 | N.S. |
| β-TG (ng/ml) | 127.8 ± 58.1 | 121.8 ± 65.2 | N.S. |
| Vu (cm/sec/mmHg) | 0.370 ± 0.064 | 0.323 ± 0.072 | 0.0297 |

Values are presented as mean ± standard deviation

APPARATUS FOR ASSESSING RISK OF CEREBROVASCULAR DISEASES

RELATED APPLICATIONS

This application is a continuation of PCT/JP2009/060630 filed on Jun. 10, 2009, which claims priority to Japanese Application No. 2008-154262 filed on Jun. 12, 2008. The entire contents of these applications are incorporated herein by reference.

BACKGROUND OF THE INVENTION

1. Field of the Invention

The present invention relates to an apparatus for assessing the risk of cerebrovascular diseases, particularly an apparatus for assessing the risk of cerebrovascular diseases by measuring the state of blood flow in a non-invasive manner.

2. Description of the Related Art

Attention has been focused on the metabolic syndrome recently. The metabolic syndrome increases the incidence of various thrombotic diseases such as cardiovascular diseases and cerebral infarction and has therefore been a social issue.

It has been known that lesions in cerebral white matter and non-symptomatic cerebral infarction caused by chronic ischemia following the consolidation of brain arteriolae are powerful risk factors of the occurrence of cerebral infarction as one of diseases in relation with cerebrovascular diseases (namely, the risk of cerebrovascular diseases). Findings about the risk of cerebrovascular diseases can be discovered by head MRI examinations (Patent Reference 1).

However, disadvantageously, MRI examinations are costly with a long scanning time and are sensitive to motions. Furthermore, disadvantageously, MRI apparatuses are not transportable or cannot make images when persons to be examined put on metal-made materials, life maintenance apparatuses, aspirators or other similar apparatuses.

PRIOR TECHNICAL REFERENCES

Patent Reference 1: JP-A-2007-105207

Based on those described above, it is an object of the invention to provide an apparatus for assessing the risk of cerebrovascular diseases with simple measuring units causing fewer burdens to persons to be examined.

SUMMARY OF THE INVENTION

An apparatus for assessing the risk of cerebrovascular diseases in accordance with the invention includes a flow rate-measuring part that measures the flow rate value of blood circulating in the vascular tube of a human subject from the outside thereof, a blood pressure-acquiring part that acquires the blood pressure value of the vascular tube, and a risk computation part of cerebrovascular diseases that assesses the risk of cerebrovascular diseases, using the blood pressure value acquired by the blood pressure-acquiring part and the flow rate value measured by the flow rate-measuring part. In accordance with the invention, the risk of cerebrovascular diseases can be assessed without any head MRI examinations.

Additionally, the apparatus for assessing the risk of cerebrovascular diseases in accordance with the invention includes an output part that outputs and displays the indicator value calculated at the risk computation part of cerebrovascular diseases. In accordance with the invention, the result of the assessment of the risk of cerebrovascular diseases can be expressed in a readily understandable manner.

Furthermore, the risk computation part of cerebrovascular diseases in the apparatus for assessing the risk of cerebrovascular diseases in accordance with the invention assesses the risk of cerebrovascular diseases, using one or plural maximal values of blood flow rate among blood flow rate values variable over time together with the maximal blood pressure value acquired by the blood pressure-acquiring part. In accordance with the invention, blood flow rate per unit pressure can be calculated. Hence, the influence of blood pressure can be excluded.

Still furthermore, the flow rate-measuring part in the apparatus for assessing the risk of cerebrovascular diseases in accordance with the invention includes a transmission part that transmits a continuous wave to the blood from the surface of the human subject, a receiving part that receives a reflection wave reflected on the blood from the transmitted continuous wave, and a rate wave form computation part that computes the flow rate value of the blood, using the frequency variation of the reflection wave along two directions as received at the receiving part. In accordance with the invention, blood flow can be measured more accurately.

Additionally, the risk computation part of cerebrovascular diseases in the apparatus for assessing the risk of cerebrovascular diseases in accordance with the invention assesses the risk of cerebrovascular diseases at a number of grades. In accordance with the invention, the level of the risk of cerebrovascular diseases can be assessed.

The risk of cerebrovascular diseases can be assessed with such simple measuring units. Since the apparatus is an apparatus with fewer burdens to patients, which is operable by persons without any specific qualification, users can set up the apparatus in their houses and the like to simply assess the risk of cerebrovascular diseases.

BRIEF DESCRIPTION OF THE DRAWINGS

FIG. 6 is a figure depicting the comparative results between the results of head MRI examinations and the results of the individual items measured.

DETAILED DESCRIPTION OF THE PREFERRED EMBODIMENTS

The apparatus for assessing the risk of cerebrovascular diseases in the present mode assesses the risk of cerebrovascular diseases, based on given calculations using blood flow rate and blood pressure.

Blood flow rate can be determined by transmitting a continuous ultrasonic wave to blood flow and determining the variation of the frequency of the reflected continuous wave (Doppler Shift). As the blood pressure, the value of blood pressure as measured with general blood pressure meters is used.

The maximal blood flow rate and the maximal blood pressure among the values obtained as described above are inputted in the following calculation formulas to calculate the blood flow rate per unit pressure by the apparatus for assessing the risk of cerebrovascular diseases. Herein, the reason why the maximal such values are used is that since the blood flow rate reaches maximum at the maximal blood pressure, corresponding values can readily be obtained among such variable values.

The apparatus for assessing the risk of cerebrovascular diseases in the mode can measure the blood flow rate per unit pressure in a non-invasive manner, to assess the risk of cerebrovascular diseases, based on the relation between the blood flow rate per unit pressure and the data of head MRI examinations. Further, the apparatus for assessing the risk of cerebrovascular diseases in the mode can be made in a small size, so users can daily know the risk of cerebrovascular diseases in their daily lives in homes to control their health in a simple fashion.

Figure 1:
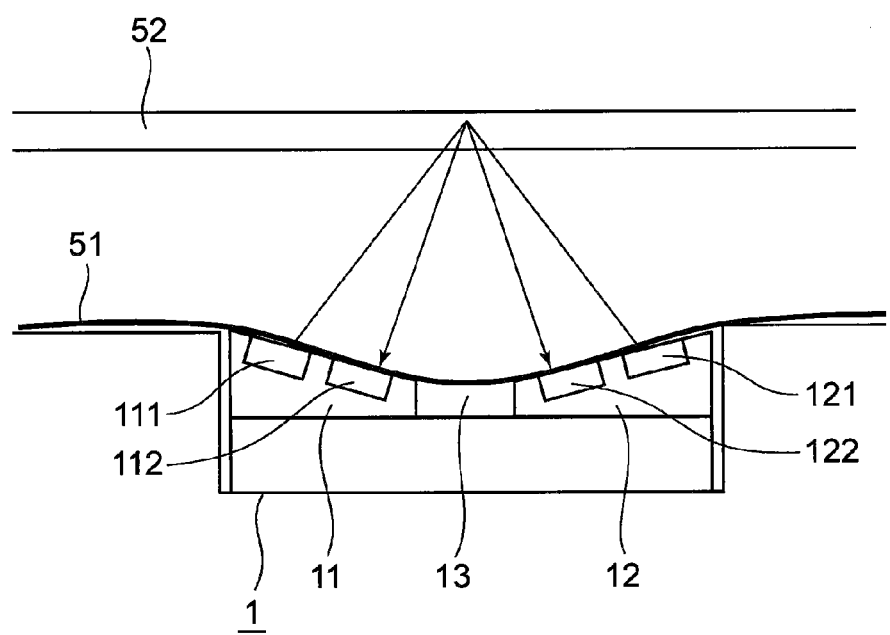
FIG. 1 is a view schematically depicting the sensor part of the apparatus for assessing the risk of cerebrovascular diseases in accordance with the invention.

FIG. 1 is a view of the sensor part of the apparatus for assessing the risk of cerebrovascular diseases, depicting the cross section of the sensor part, together with skin 51 and vascular tube 52 arranged with the sensor part 1.

The sensor part 1 is a sensor sensing blood flow rate, which is arranged for example on human wrists, finger tips and arms. More specifically, for example, the sensor part 1 is structurally formed in a sack shape, which is inserted onto a finger tip of a user. Otherwise, the sensor part 1 is structurally mounted on a belt; and the belt may then be arranged on wrists or arms.

Furthermore, the sensor part 1 and a measuring system described below may also be integrated in a wrist watch. In this case, the wrist watch is switched between the time measuring mode and the mode for assessing the risk of cerebrovascular diseases. A user with the wrist watch on can assess the risk of cerebrovascular diseases by the mode for assessing the risk of cerebrovascular diseases.

The sensor part 1 includes a basal part 13, and a first ultrasonic sensor 11 including a transmission device 111 and a receiving device 112, and a second ultrasonic sensor 12 including a transmission device 121 and a receiving device 122. The transmission devices 111 and 121 compose wave transmission devices, while the receiving devices 112 and 122 compose wave receiving devices.

The basal part 13 is composed of a solid matter such as resin to retain the first ultrasonic sensor 11 and the second ultrasonic sensor 12 at predetermined positions on a face along a direction in contact with human bodies.

The individual devices composing the first ultrasonic sensor 11 and the second ultrasonic sensor 12 are all composed of piezoelectric devices for use in ultrasonic transmission and reception and for use in measuring blood flow rate.

At the first ultrasonic sensor 11, more specifically, the transmission device 111 transmits a continuous ultrasonic wave (simply referred to as continuous wave hereinafter) into a biological organism. The continuous wave is reflected on blood flow circulating in the vascular tube 52 and is then received with the receiving device 112.

The frequency of the reflected continuous wave is variable due to the Doppler Effect from blood flow rate. Using the variation of the frequency (Doppler Shift), the blood flow rate can be determined.

At the second ultrasonic sensor 12, similarly, the continuous wave transmitted from the transmission device 121 is reflected on blood flow circulating in the vascular tube 52 and is then received with the receiving device 122.

The first ultrasonic sensor 11 and the second ultrasonic sensor 12 are fixed at given angles on the basal part 13 to transmit a continuous wave to the vascular tube 52 along different directions. In such manner, the angle of the sensor part 1 to the vascular tube 52 can be calculated, to more accurately calculate blood flow rate.

Provided that the angle of the first ultrasonic sensor 11 to the vascular tube 52 is defined as "θ"; the angle of the first ultrasonic sensor 11 to the second ultrasonic sensor 12 is defined as "α"; the variation of the frequency as detected with the first ultrasonic sensor 11 is defined as Δf1; and the variation of the frequency as detected with the second ultrasonic sensor 12 is defined as Δf2, these variations can be given by the following formulas (1) and (2).

$$\Delta f1 = 2 \times v \times \cos\theta \times F \div c \quad (1)$$

$$\Delta f2 = 2 \times v \times \cos(\theta + \alpha) \times F \div c \quad (2)$$

In the formulas (1) and (2), "c" is the sonic speed in biological organisms and is about 1530 m/s. Further, "F" expresses the frequency of an ultrasonic wave transmitted into biological organisms, while "v" expresses blood flow rate. Based on the formulas (1) and (2), "θ" is expressed by the following formula (3).

$$\tan\theta = [\Delta f2 + \Delta f1 - \cos(\theta + \alpha + \beta)] \div c \quad (3)$$

An adjustment part is arranged on the faces of the first ultrasonic sensor 11 and the second ultrasonic sensor 12 on their sides of transmitting and receiving ultrasonic wave. The adjustment part is composed of ultrasonic wave-transmitting media such as resin and composes an acoustic adjustment layer adjusting the impedance between the sensor part 1 and the inside of biological organisms. More specifically, the adjustment part is preferably composed of a medium at an impedance level intermediately between the impedance of the transmission and receiving devices and the impedance of the inside of biological organisms.

By reducing the change of the impedance in the transmission pathway of ultrasonic wave, as described above, the ultrasonic reflection between the sensor part 1 and the inside of biological organisms can be reduced, to improve the ultrasonic transmission efficiency.

Using the block diagram of FIG. 2, then, the system structure of the apparatus for assessing the risk of cerebrovascular diseases is now described below.

Figure 2:
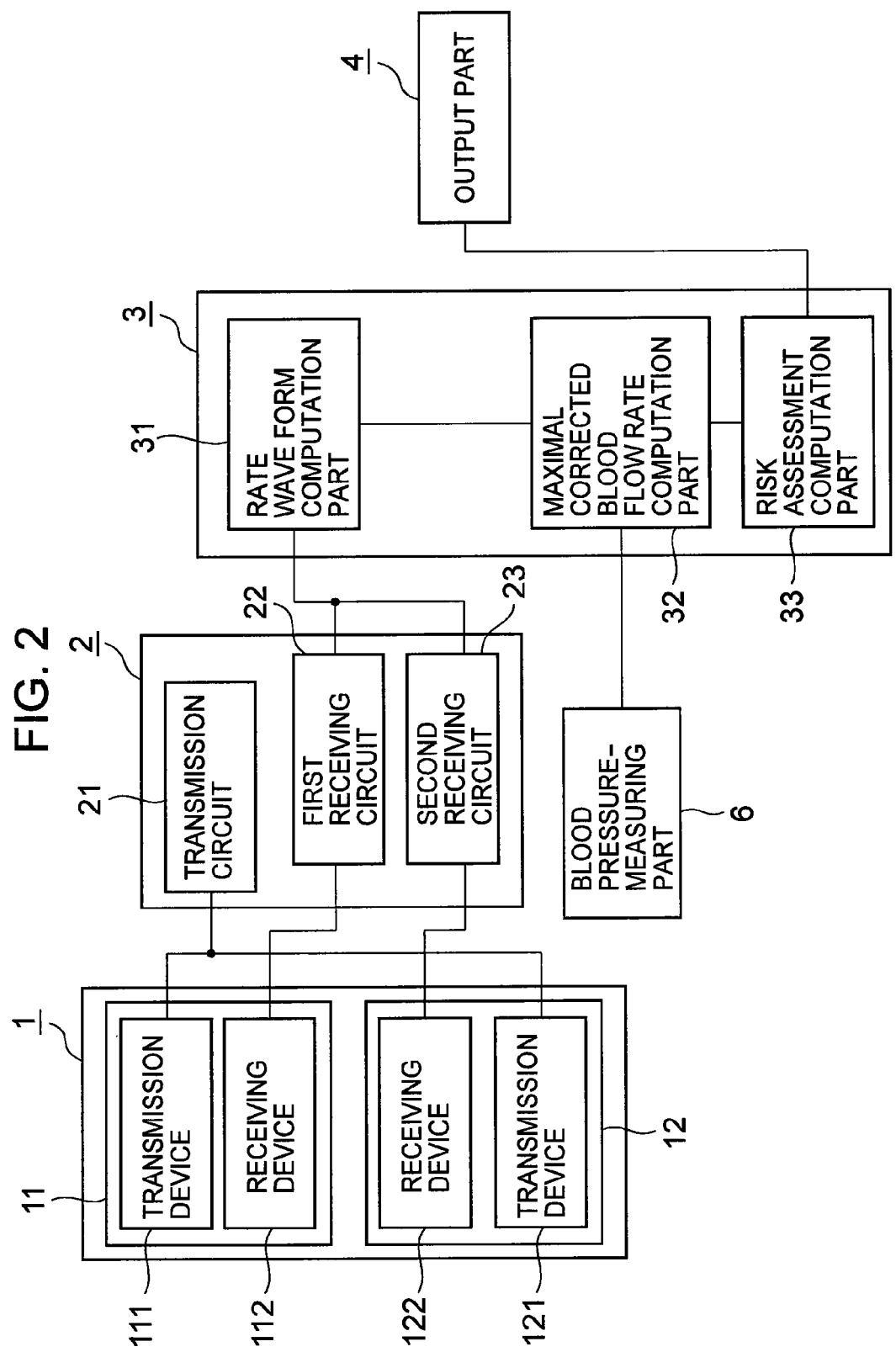
FIG. 2 is a block diagram for describing the structure of the apparatus for assessing the risk of cerebrovascular diseases in accordance with the invention.

As shown in FIG. 2, the apparatus for assessing the risk of cerebrovascular diseases in the mode includes a sensor part 1, a circuit part 2, a computation part 3 and an output part 4.

Because the sensor part 1 is already described, the circuit part 2, the computation part 3 and the output part 4 are now described herein.

The circuit part 2 is a functional part for driving the sensor part 1 and transmitting a signal detected at the sensor part 1 to the computation part 3. The circuit part 2 includes a transmission circuit 21, a first receiving circuit 22, a second receiving circuit 23 and the like.

The transmission circuit 21 is in connection with the transmission device 111 and the transmission device 121. By driving these devices, the transmission circuit 21 generates a continuous wave. The frequency of a continuous wave driven by the transmission circuit 21 is generally about 10 to 20 MHz.

Characteristically, the resolution of an ultrasonic wave is higher as the frequency of the ultrasonic wave is higher. In that case, however, the distance of the ultrasonic wave to invade into biological organisms gets shorter. When the frequency thereof is lower, the distance thereof to invade into biological organisms is longer while the resolution thereof is lower. Taking account of these characteristic profiles, an appropriate frequency is selected.

The first receiving circuit 22 is in connection with the receiving device 112, to receive the reflected continuous wave of a continuous wave outputted from the transmission device 111, for outputting to the computation part 3.

The second receiving circuit 23 is in connection with the receiving device 122, to receive the reflected continuous wave of a continuous wave outputted from the transmission device 121, for outputting to the computation part 3.

Not shown in the figure, filters are arranged individually between the receiving device 112 and the circuit part 2 and between the receiving device 122 and the circuit part 2, which work for preventing the reception of reflected wave from transmission devices except the corresponding transmission devices.

The computation part 3 includes a rate wave form computation part 31, a blood flow rate computation part 32, a risk assessment part 33 and the like.

Figure 3:
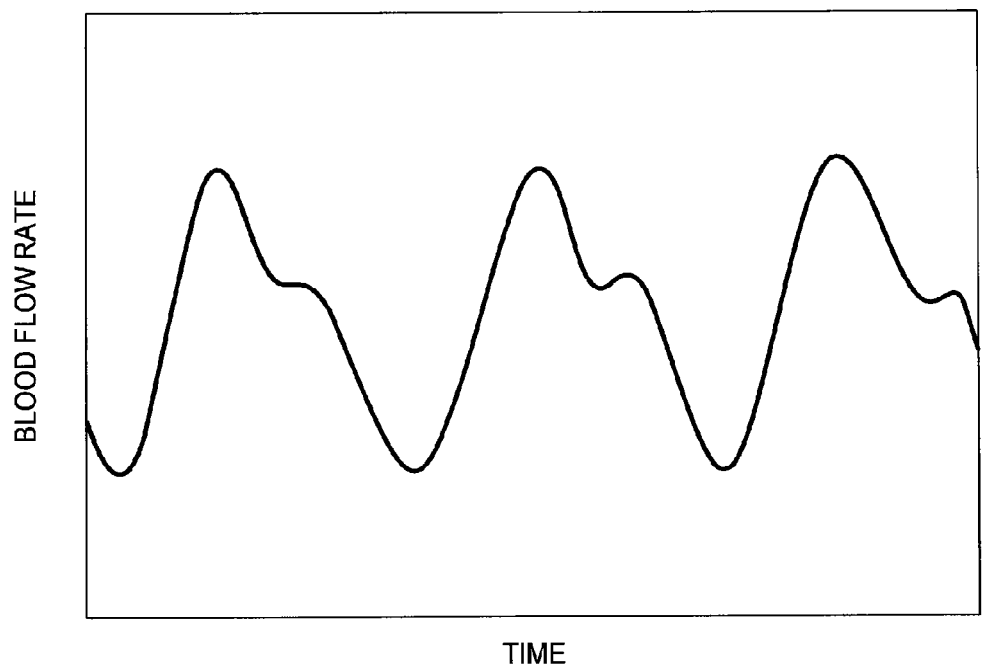
FIG. 3 is a chart depicting the wave form of blood flow rate as obtained by the apparatus for assessing the risk of cerebrovascular diseases in accordance with the invention.

The rate wave form computation part 31 is in connection with the first receiving circuit 22 and the second receiving circuit 23, to obtain the frequency of the reflected continuous wave detected with the receiving devices 112, 122. Comparing the frequency with the frequency from the transmission circuit 21, then, the variations of the frequency, namely Δf1 and Δf2 in the formulas (1) and (2), respectively can be detected. By substituting these values in the formula (3), "θ" can be calculated. Thus, the blood flow rate "v" can be determined by the formulas (1) and (2), so that the wave form shown in FIG. 3 can be obtained. In FIG. 3, the horizontal axis expresses time; and the vertical axis expresses blood flow rate (the rate of blood flow). Herein, the sensor part 1, the circuit part 2 and the rate wave form computation part 31 compose the flow rate-measuring part.

The blood flow rate computation part 32 obtains blood flow rate data from the rate wave form computation part 31 and additionally obtains blood pressure data from the blood pressure-measuring part 6, to calculate blood flow rate.

The risk assessment computation part 33 composes a risk computation part of cerebrovascular diseases for assessing the risk of cerebrovascular diseases, using these data.

At the blood pressure-measuring part 6, a user inputs a value measured by using general blood pressure meters. Therefore, the blood pressure-measuring part 6 may be equipped with user interfaces such as key board for inputting numerical figures into the computation part 3. Otherwise, the computation part 3 may be in connection through an interface with a blood pressure meter.

In the mode, the apparatus is in a structure such that maximal blood pressure is used to assess the risk of cerebrovascular diseases, as described below. Therefore, maximal blood pressure is at least inputted as the blood pressure data. As described above, the blood flow rate computation part 32 includes such a blood pressure acquisition unit as described above.

As shown in FIG. 3, the flow rate detected at the rate wave form computation part 31 beats up and down following the pulsation of heart.

The blood flow rate computation part 32 obtains the maximal flow rate "Vmax" from the flow rate data obtained from the rate wave form computation part 31. The maximum flow rate for obtaining "Vmax" is any of the maximum flow rates detected. Furthermore, the maximum flow rates are retrieved from the flow rate data. By subsequently averaging the flow rates, the resulting average may be used as "Vmax".

Since it is understood that the blood pressure when the blood flow rate is "Vmax" is maximal blood pressure, the blood flow rate computation part 32 defines maximal blood pressure obtained by the blood pressure-measuring part 6 as blood pressure "Pmax" when "Vmax" is obtained.

Because blood flow rate and blood pressure are separately measured in this mode, it is not needed to take account of the change of blood flow rate due to blood pressure measurement.

Because blood flow changes due to the pressurization of arms and the like when blood pressure is measured, blood pressure and blood flow rate are preferably measured with a time lag interval, as described above.

At the blood flow rate computation part 32, "Vmax" and "Pmax" obtained in such manner are substituted in the following formula (4), to calculate the blood flow rate "Vu" per unit pressure.

$$Vu = Vmax \div Pmax \quad (4)$$

In the calculation of the formula (4), the maximum values of blood flow rate and blood pressure are used. The reason is that the use of such maximum values enables ready acquisition of corresponding blood flow rate and blood pressure. Specifically because blood pressure is maximal when blood flow rate is maximal, the blood pressure at the maximum blood flow rate is defined as the maximum blood pressure. The formula (4) is a formula generally established when the values are not such maximum values. When blood pressure is determined at a certain blood flow rate, these values are substituted in the formula (4) to determine the blood flow rate per unit pressure.

So as to assess the risk of cerebrovascular diseases in such manner, the computation part 3 includes hardware for example CPU (Central Processing Unit), ROM (Read Only Memory), RAM (Random Access Memory), and EEPROM (Electrically Erasable and Programmable ROM).

CPU is a central processing unit for various computation processes, controlling the whole computation part 3, and controlling data transmission and reception between the circuit part 2 and the output part 4, according to programs memorized in ROM, RAM, EEPROM and the like.

ROM is essentially a read only memory memorizing parameters and programs for functionally operating the computation part 3. Using these parameters and programs, CPU sets up the apparatus for assessing the risk of cerebrovascular diseases to the initial state when the apparatus is started.

RAM is a memory medium capable of random access memory. For CPU assessing the risk of cerebrovascular diseases, RAM provides an area for obtaining and memorizing data from the receiving circuit 22, the receiving circuit 23, the blood pressure-measuring part 6 and the like and also provides a working area for assessing the risk of cerebrovascular diseases, using the data memorized in these areas.

EEPROM is ROM capable of rewriting or erasing data via electric manipulations in later dates.

In the mode, OS (Operating System) as a basic program for functionally operating the computation part 3, a calculation program for assessing the risk of cerebrovascular diseases and the like are memorized in EERPOM.

CPU is composed of software of individual functional parts such as a rate wave form computation part 31, a blood flow rate computation part 32 and a risk assessment computation part 33, for the execution of calculation programs.

Additionally, the computation part 3 may also be composed of a memory medium of a large capacity such as hard disk, to accumulate daily blood flow rate data, blood pressure data and the indicator value of a user.

Still additionally, the computation part 3 may also be composed of input and output interfaces to output blood flow rate data and blood pressure data to an outside computer or to read data and programs from the outside.

The computation part 3 may also be composed of a memory medium-driving apparatus for driving an outer memory medium composed of flexible disks, magneto-optical disks, and semiconductor memories, to write data about platelet activation level and blood flow data on these outer memory media or to read data and programs written on the outer memory media.

Those described above represent just one example of the hardware structure of the computation part 3, with no limitation to the structure of the computation part 3. The computation part 3 may satisfactorily be in any structure including the rate wave form computation part 31, the blood flow rate computation part 32 and the risk assessment computation part 33.

Furthermore, the sensor part 1 outputs analog data while the computation part 3 processes digital data. Therefore, analog data should necessarily be sampled and converted to digital data at some stage. Structurally, the conversion may be done at the circuit part 2 or at the computation part 3.

Figure 4:
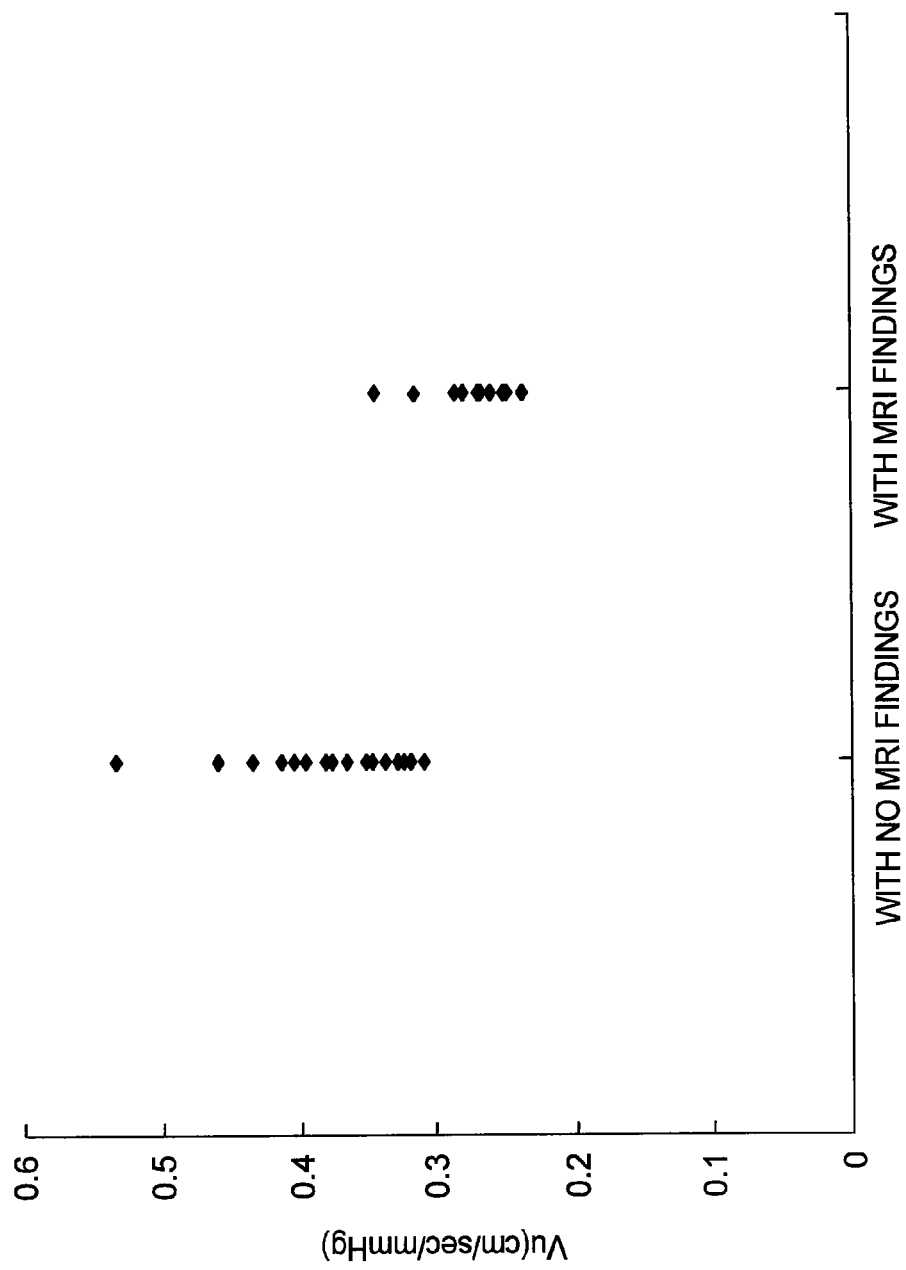
FIG. 4 shows graphs depicting the correlation between the blood flow rate "Vu" and the results of head MRI examinations.
Figure 5:
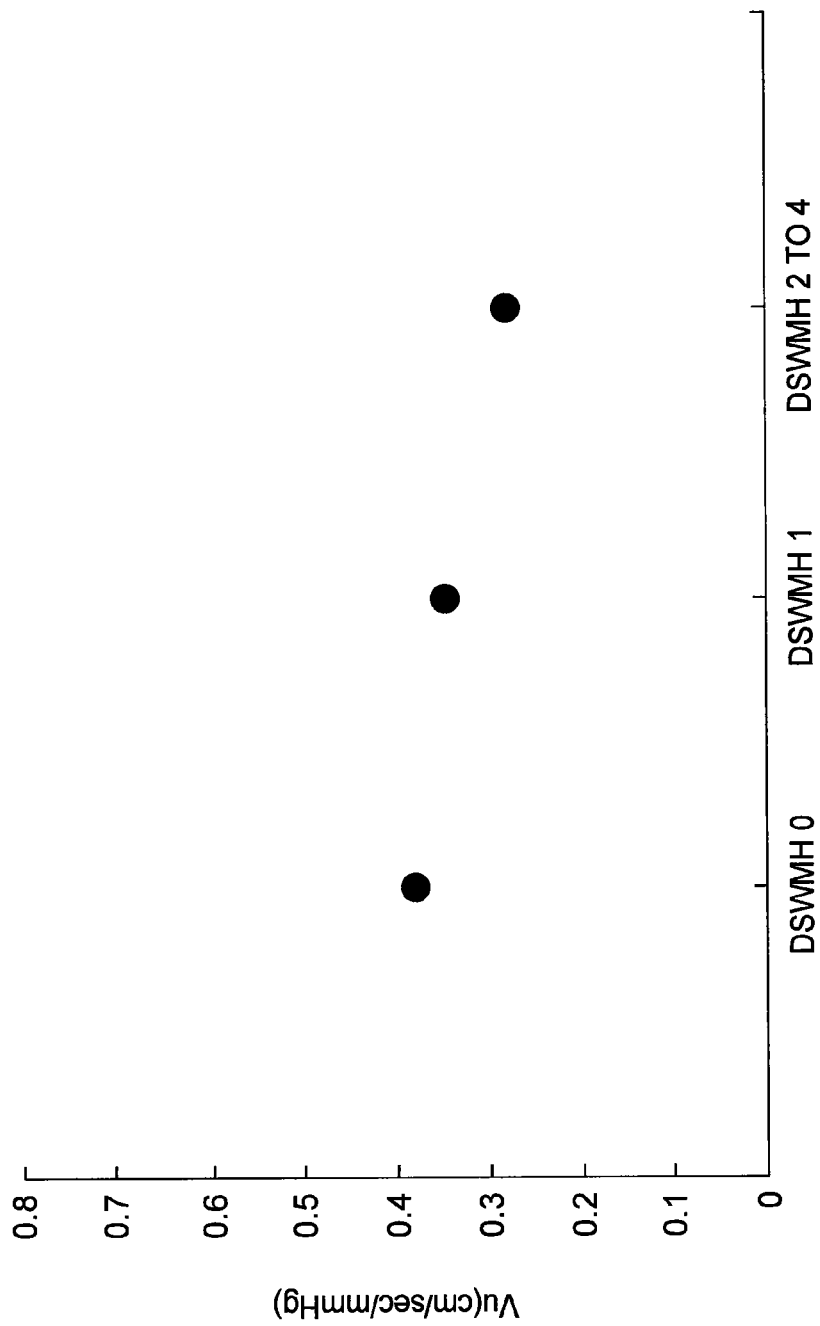
FIG. 5 shows graphs depicting the correlation between the blood flow rate "Vu" and the results of head MRI examinations.

Then, the output part 4 is now described below. The output part 4 is equipped with a part for displaying results, not shown in figures, to display data outputted from the risk assessment computation part 33. For more detailed description, FIGS. 4 and 5 are used. The risk of cerebrovascular diseases may be assessed at the risk assessment computation part 33. The display apparatus is composed of for example liquid crystal display, plasma display or CRT display, for displaying the value of platelet activation level in numerical figure. Furthermore, the value thereof may also be displayed, using graphs or symbols.

FIG. 4 is a view depicting the correlation between the blood flow rate "Vu" per unit pressure as measured by the apparatus for assessing the risk of cerebrovascular diseases and the results obtained by head MRI examinations. In FIG. 4, the vertical axis expresses the blood flow rate "Vu" per unit pressure in accordance with the invention while the horizontal axis expresses the presence or absence of findings indicating the risk of cerebrovascular diseases by head MRI examinations (non-symptomatic cerebral infarction or lesions in cerebral white matter). In a group with the head MRI findings, "Vu" is significantly reduced. The blood flow rate per unit pressure as determined by the apparatus in accordance with the invention varies depending on the presence or absence of findings in the results by head MRI examinations. Hence, the risk of cerebrovascular diseases can be assessed.

FIG. 5 is a view depicting the correlation between the blood flow rate "Vu" per unit pressure as measured by the apparatus for assessing the risk of cerebrovascular diseases and the results obtained by head MRI examinations. In FIG. 5, the vertical axis expresses the blood flow rate "Vu" per unit pressure in accordance with the invention while the horizontal axis expresses the grades of deep subcortical white matter hyperintensity (DSWMH) (grades of 0 to 4; a larger grade expresses progressed conditions of the disease) as one of lesions in cerebral white matter in head MRI examinations, where the average "Vu" is expressed per grade. At a larger grade of deep subcortical white matter hyperintensity (DSWMH), "Vu" is lower. As described above, the blood flow rate "Vu" per unit pressure as determined by using the apparatus of the invention is in correlation with the grade of deep subcortical white matter hyperintensity. Accordingly, the risk of cerebrovascular diseases may be assessed at such grades.

FIG. 6 shows the comparative results between the results of head MRI examinations and the results of individual items measured. Cases observed with findings about the risk of cerebrovascular diseases (non-symptomatic cerebral infarction or lesions in cerebral white matter) at head MRI examinations are defined as "the group with MRI findings". Only the result obtained by using the apparatus for assessing the risk of cerebrovascular diseases in the mode significantly correlates with the presence or absence of MRI findings but never significantly correlates with the remaining items measured. Thus, the efficacy of the apparatus is demonstrated in the figure.

In the mode, further, ultrasonic wave is used for measuring blood flow rate. The wave for such measurement is not limited to ultrasonic wave. Using for example other wave types such as laser, the measurement may also be done.

What is claimed is:

1. An apparatus for assessing risk of cerebrovascular disease, comprising:
   a blood flow rate-measuring part for measuring flow rate value of blood circulating in a vascular tube of skin of a human subject from outside thereof by transmitting a continuous ultrasonic wave to blood flow, receiving one or more signals reflected from the blood flow and determining one or more variations in frequency between the transmitted continuous ultrasonic wave and the received one or more signals to determine the flow rate of blood,
   a blood pressure acquiring part for acquiring a blood pressure value of the vascular tube,
   a risk computation part of cerebrovascular diseases for assessing the risk of cerebrovascular diseases, using a maximal blood pressure value acquired at the blood pressure-acquiring part and using one or plural maximal blood flow rate values among blood flow rate values variable over time measured at the blood flow-rate measuring part, wherein the risk computation part assesses the risk by determining a value for blood flow rate per unit pressure as a ratio of the one or plural maximal blood flow rate values and the maximal blood pressure value, wherein the risk computation part assesses the risk of cerebrovascular diseases at a number of grades of deep subcortical white matter hyper-sensitivity based on a correlation between grades of deep subcortical white matter hypersensitivity and blood flow rates per unit pressure using results obtained by prior head magnetic resonance imaging (MRI) examinations of human subjects other than the human subject; and
   an output part including a display apparatus to display an indicator corresponding to the risk of cerebrovascular diseases as assessed by the risk computation part without invasive procedure or MRI examination of the human subject.

2. An apparatus for assessing the risk of cerebrovascular diseases according to claim 1, wherein the output part is configured for outputting and displaying an indicator value calculated by the risk computation part of cerebrovascular diseases.

3. An apparatus for assessing the risk of cerebrovascular diseases according to claim 1, wherein the blood flow rate-measuring part comprises a transmission part for transmitting the continuous ultrasonic wave from a surface of the human subject to the blood, a receiving part for receiving a reflection wave reflected on the blood from the transmitted continuous ultrasonic wave, and a rate wave form computation part for calculating the flow rate value of the blood, using variations of frequency of the reflection wave along two directions as received at the receiving part.

4. An apparatus for assessing the risk of cerebrovascular diseases according to claim 2, wherein the blood flow rate-measuring part comprises a transmission part for transmitting the continuous ultrasonic wave from a surface of the human subject to the blood, a receiving part for receiving a reflection wave reflected on the blood from the transmitted continuous ultrasonic wave, and a rate wave form computation part for calculating the flow rate value of the blood, using variations of frequency of the reflection wave along two directions as received at the receiving part.

5. An apparatus for assessing the risk of cerebrovascular diseases according to claim 1 wherein the blood flow rate-measuring part is configured to:

determine a second variation in frequency along a second axis between the transmitted ultrasonic wave and a first received signal;

determine a second variation in frequency along a first axis between the transmitted ultrasonic wave and a second received signal; and using the first variation in frequency and the second variation in frequency, determine the flow rate value of blood.

6. An apparatus for assessing the risk of cerebrovascular diseases according to claim 1 wherein the display apparatus comprises one or more of a liquid crystal display, a plasma display and a cathode ray tube (CRT) to display the indicator corresponding to the risk of cerebrovascular diseases in numerical figures.

7. An apparatus for assessing the risk of cerebrovascular diseases according to claim 1 wherein the risk computation part is operative to determine data about platelet activation level; and wherein the display apparatus comprises one or more of a liquid crystal display, a plasma display or a cathode ray tube (CRT) display to display a value of platelet activation level in numerical figures.

* * * * *

UNITED STATES PATENT AND TRADEMARK OFFICE
CERTIFICATE OF CORRECTION

PATENT NO.         : 9,554,769 B2
APPLICATION NO.    : 12/963292
DATED              : January 31, 2017
INVENTOR(S)        : Tsutomu Kamei et al.

It is certified that error appears in the above-identified patent and that said Letters Patent is hereby corrected as shown below:

In the Claims

In Column 8, Claim 1, Line 27, before "comprising:" replace "disease," with --diseases,--.

In Column 8, Claim 1, Line 36, before "of blood," insert --value--.

In Column 8, Claim 1, Lines 44-45, after "measured at the blood" replace "flow-rate measuring" with --flow rate-measuring--.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*